United States Patent

Müller et al.

[11] Patent Number: 5,866,673
[45] Date of Patent: Feb. 2, 1999

[54] POLYMERIZABLE DERIVATIVES OF POLYAMIDES

[75] Inventors: Egbert Müller, Erzhausen; Anja Seiler, Gross-Zimmern; Roland Gensert, Seeheim, all of Germany

[73] Assignee: Merck Patent Gesellschaft mit Beschrankter Haftung, Germany

[21] Appl. No.: 875,276

[22] PCT Filed: Jan. 10, 1996

[86] PCT No.: PCT/EP96/00077

§ 371 Date: Jul. 21, 1997

§ 102(e) Date: Jul. 21, 1997

[87] PCT Pub. No.: WO96/22316

PCT Pub. Date: Jul. 25, 1996

[30] Foreign Application Priority Data

Jan. 20, 1995 [DE] Germany .......... 195 01 726.9

[51] Int. Cl.⁶ .......... C08G 69/48; C08L 77/00
[52] U.S. Cl. .......... 528/310; 528/314; 528/315; 528/317; 528/318; 528/323; 528/335; 528/345; 525/178; 525/181; 525/426; 525/432

[58] Field of Search .......... 528/318, 314, 528/315, 317, 323, 310, 335, 345; 525/178, 181, 426, 432

[56] References Cited

U.S. PATENT DOCUMENTS

| | | | |
|---|---|---|---|
| 4,595,730 | 6/1986 | Blondel et al. | 525/178 |
| 4,874,817 | 10/1989 | Inskip et al. | 525/183 |
| 5,177,144 | 1/1993 | Torres et al. | 525/181 |
| 5,326,830 | 7/1994 | Aharoni | 525/181 |

*Primary Examiner*—P. Hampton-Hightower
*Attorney, Agent, or Firm*—Miller, White, Zelano, & Branigan, P.C.

[57] ABSTRACT

The invention relates to polymerisable double-bond derived polyamides obtainable by reacting the polyamide in an aqueous solution with a compound which contains both a polymerisable double bond and an oxirane ring. These derived polyamides may be processed to provide graft polymers with improved properties.

17 Claims, No Drawings

POLYMERIZABLE DERIVATIVES OF POLYAMIDES

The invention relates to polymerizable derivatives of polyamides, to processes for graft polymerization on such derivatized polyamides and finally to graft polymers and shaped articles produced by these processes.

By means of grafting reactions it is possible to modify the surfaces of polymers and of shaped articles made from polymers, making it possible to attain properties which are not achievable with the base polymer alone.

Various processes for carrying out grafting reactions are known. Such processes, together with their advantages and disadvantages, are discussed in detail, for example, in WO 91/03 506. For example, the grafting can be carried out using excitation with high-energy radiation, but undesirable side-reactions occur with this: degradation of the polymer chains, which impairs the mechanical strength of the polymers, and crosslinking reactions which lead to embrittlement of the material. Other processes of graft polymerization require the use of a strongly acid medium, but polyamides are partially hydrolyzed during these. Still further processes for graft polymerization are based on chain transfer, where a free-radical initiator induces a homopolymerization of the monomer in the presence of the base polymer which is to be grafted. The grafting location cannot be controlled as desired.

WO 91/03 506 describes a process for grafting onto polyamide membranes, in which the free-radical reaction is initiated by treating with carbon tetrachloride in the presence of a reducing agent. In this process, the free-radical chain is initiated via an un-known reaction mechanism starting from a haloamide. It is known from the literature that haloamides are very reactive. This can lead to undesired reactions, such as the covalent binding of proteins when a derivatized membrane is used. In addition, the use of reducing agents impairs the mechanical properties of the polyamide.

It is an object of the invention to provide a process for the targeted derivatization of polyamides. These derivatized polymers can then be reacted further by known processes. The derivatized polyamides which are provided should retain their mechanical properties to a sufficient extent that these processes are applicable, for example, even for hollow-fiber membranes.

The invention relates to polyamides which are derivatized with polymerizable double bonds and are obtainable by reacting the polyamide with a compound which comprises both a polymerizable double bond and also an oxirane ring. Compounds of the formula I are preferred as compounds which comprise both a polymerizable double bond and also an oxirane ring:

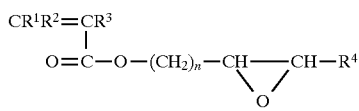

where $R^1$, $R_2$ and $R^3$ independently of one another are H or $CH_3$, $R^4$ is H, alkyl with from 1 to 5 carbon atoms or aryl with from 6 to 12 carbon atoms and n is an integer from 1 to 5.

The invention also relates to graft polymers obtainable by polymerization of monomers onto, as base polymer, a polyamide derivatized according to the invention with polymerizable double bonds.

Particular preference is given to graft polymers which comprises monomer units of the formula II, III, IV or V:

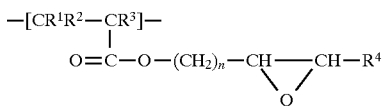

where:

$R^1$, $R^2$ and $R^3$ independently of one another are H or $CH_3$, $R^4$ is H, alkyl with from 1 to 5 carbon atoms or aryl with from 6 to 12 carbon atoms and n is an integer from 1 to 5.

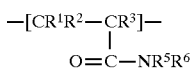

where $R^1$, $R^2$ and $R^3$ independently of one another are H or $CH_3$, $R_5$ is H, or alkyl with from 1 to 5 carbon atoms substituted with —COOH, with —$SO_3H$ or with $NR^7R^8$, or aryl with from 6 to 12 carbon atoms and substituted with —COOH, —$SO_3H$ or with —$NR^7R^8$, $R_6$ is alkyl with from 1 to 5 carbon atoms substituted with —COOH, with —$SO_3H$ or with $NR^7R_8$, or aryl with from 6 to 12 carbon atoms and substituted with —COOH, —$SO_3H$ or with —$NR^7R^8$, where $R_5$ and $R^6$ are selected so that either both radicals are acid or basic or one of the radicals is neutral, and $R_7$ and $R_8$ independently of one another are H or alkyl with from 1 to 5 carbon atoms.

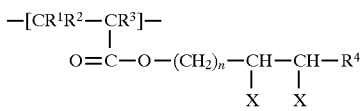

where:

$R^1$, $R_2$ and $R^3$ independently of one another are H or $CH_3$, $R^4$ is H, alkyl with from 1 to 5 carbon atoms or aryl with from 6 to 12 carbon atoms, n is an integer from 1 to 5, one radical X is a separation effector and the other radical X is OH.

The separation effector may in particular be one of the following:

a) an ionic radical selected from the group consisting of —$PO_4H_2$, —$NR^7R_8$ and $N^+R^7R^8R^9$, where $R^7$ and $R^8$ independently of one another are H or alkyl with from 1 to 5 carbon atoms and $R^9$ is alkyl with from 1 to 5 carbon atoms with the proviso that if X=$N^+R^7R^8R^9$, $R^7$ and $R^8$ may not be H, b) a hydrophobic moiety —$OR^{10}$ or —$NHR^{10}$, where $R^{10}$ is $C_1$–$C_{20}$-alkyl, $C_6$–$C_{25}$-aryl, $C_7$–$C_{25}$-alkylaryl or $C_7$–$C_{25}$-arylalkyl, and where these radicals may also be derivatized with nitrile or $C_1$–$C_5$-alkoxy, and where, furthermore, one or more non-adjacent $CH_2$ radicals may also be replaced by NH or O or else one or more CH radicals may be replaced by N;

c) a metal chelate moiety;

d) a thiophilic radical.

Thiophilic radicals are disclosed, for example, in EP 0 165 912.

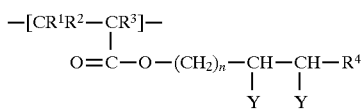

where:

R$^1$, R$^2$ and R$^3$ independently of one another are H or CH$_3$,

R$^4$ is H, alkyl with from 1 to 5 carbon atoms or aryl with from 6 to 12 carbon atoms, n is an integer from 1 to 5, one radical Y is a radical of formula VI and the other radical Y is OH

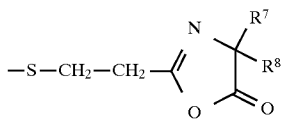

and

R$^7$ and R$^8$ independently of one another are H or alkyl with from 1 to 5 carbon atoms.

In particular the graft polymers which have monomer units of the formula II or V can be used for preparing affinity supports or for immobilizing enzymes.

The invention therefore also relates to affinity supports and immobilized enzymes which can be prepared from a graft polymer of the invention.

Porous and non-porous shaped articles made from polyamides are known; examples are membranes, sponges, tubes and hollow-fiber membranes. The invention therefore also relates to shaped articles of this type which consist essentially of a graft polymer of the invention and which may additionally comprise affinity ligands or immobilized enzymes.

According to the invention, in the first reaction step unsaturated radicals are introduced into the polyamide. Suitable polyamides are known to the person skilled in the art and are also commercially available. Examples are the polymers known under the trade name NYLON®, such as NYLON® 66. Porous and non-porous shaped articles consisting of polyamides of this type are likewise known and also commercially available; examples are bead-form shaped articles, membranes, tubes, hollow-fiber membranes and sponges. The polyamide which is to be derivatized is reacted with a compound which comprises both an unsaturated C=C moiety and an oxirane ring. It was found that this reaction can be carried out in an excellent manner without the addition of halohydrocarbons or reducing agents. The reaction is carried out in aqueous-organic solution at a pH>5. Particularly preferred organic solvents are dimethylformamide (DMF), dimethylsulfoxide (DMSO) and dioxane. The proportion of the organic solvent here is typically greater than, 30 percent by weight. It is also possible to carry out the reaction in pure organic solvent. If the reaction is carried out at a pH>10, it is also possible to work in purely aqueous phase. For a surface which is to be derivatized of 100 cm$^2$, the reaction typically uses from 1 to 20 g of a compound which comprises both an unsaturated C=C moiety and also an oxirane ring, such as glycidyl methacrylate, dissolved in from 50 to 500 ml of solvent. The reaction is typically carried out at from 30 to 60° C., and typically takes from 30 minutes to a number of hours. In media comprising water, a buffer may be added to adjust pH; The buffer concentration is typically from 10 mM to 2M. Suitable buffers are known to the person skilled in the art; examples are borate and carbonate buffers. The reaction in purely aqueous solution can also be carried out in a dilute solution of an alkali metal hydroxide (e.g. from 0.1 to 2M sodium hydroxide or potassium hydroxide solution). Additions of a halohydrocarbon or of a reducing agent are not necessary and are not intended according to the invention.

Compounds which comprise both an unsaturated C=C moiety and also an oxirane ring are known to the person skilled in the art; examples are in particular glycidyl methacrylate, glycidyl acrylate, vinyl glycidyl ether and vinyl glycidyl urethane. Glycidyl methacrylate is preferably used.

By reacting the polyamide with a compound which comprises both an unsaturated C=C moiety and also an oxirane ring, unsaturated C=C moieties are introduced into the polyamide in a very gentle manner. Further monomers can be polymerized onto these moieties by generally known processes. The selection of these monomers depends on the intended application of the derivatized membrane:

a) DE 38 11 042 discloses, inter alia, monomers suitable for preparing ion exchangers; examples are acrylic acid, N-(sulfoethyl)acrylamide, 2-acrylamido-2-methylpropanesulfonic acid, N, N-dimethylaminoethylacrylamide, N, N-diethylaminoethylacrylamide and trimethylammoniumethylacrylamide.

Other monomers named in this publication make it possible to bind affinity ligands or enzymes, or are suitable for reversed phase chromatography; examples are acrylic acid, acrylamide, allylamine and acrylonitrile.

b) DE 43 10 964 discloses monomers which comprise an oxirane ring, an azlactone ring or a moiety which can be converted into an azlactone ring. Polymers which comprise monomers of this type are particularly effective for binding affinity ligands or enzymes. Affinity ligands are disclosed, for example, in DE 43 10 964.

The epoxide groups in the polymers of this type can, furthermore, be advantageously further reacted to give ion exchangers, thiophilic sorbents or sorbents for metal chelate chromatography or hydrophobic chromatography. In such reactions, phosphoric acid, diethylamine, trimethylamine, sulfurous acid or else complex-forming compounds, such as iminodiacetic acid are added onto the oxirane ring.

The preparation of thiophilic sorbents and of sorbents for metal chelate chromatography is disclosed in DE 43 10 964.

DE 43 33 674 and DE 43 33 821 disclose reactions of this type which can be used to prepare ion exchangers.

DE 43 23 913 describes sorbents for hydrophobic interaction chromatography.

According to the invention, the groups which are introduced into the chromatographic support by the abovementioned processes and which are significant for the separation of the analytes, are collectively referred to as separation effectors.

Details of the preparation of the various sorbents and their use can be found in the abovementioned publications; the relevant disclosure in these publications is incorporated into the present application by reference.

According to the invention, the various moieties which bring about the separation of the analytes are brought together under the term separation effectors. Examples can be seen in the abovementioned publications.

The reaction in which further monomers are polymerized onto the polyamide derivatized according to the invention may be carried out with stirring, with recirculation-pumping or through-pumping of the reaction solution. In the case of recirculation-pumping, the reaction solution is recycled and pumped through again after flowing through the polyamide membrane, while in through-pumping the reaction solution is discarded after flowing through the polyamide membrane. The latter version of the process is preferred.

The membranes derivatized and grafted in accordance with the invention, which comprise separation effectors, can be used for separation of substances in a manner which is similar to that usual, for example, with particulate sorbents having similar separation effectors. The short residence times on the sorbent reduce the risk that the biological activity, in particular, is reduced during this process. An example of applications of this type is the isolation of natural or recombinant enzymes from raw extracts. Thus, for example, the isolation of glucose dehydrogenase from Bacillus megaterium or of proteinase K from Tritirachium album includes a chromatographic step on a sorbent having ternary amino groups (e.g. DEAE) or having quaternary ammonium groups (e.g. TMAE). For the isolation of polyclonal or monoclonal immunoglobulins, such as IgG or IgM, depending on the isoelectric point of the immunoglobulin, anion or cation exchangers (e.g. having TMAE or $SO_3$ groups), but in particular also thiophilic or hydrophobic supports are used. The retention of the biological activity is of decisive importance in the isolation of clotting factors or other active ingredients of blood plasma or blood serum. Thus in the isolation of prothrombin complex or of $\alpha_1$-antitrypsin, chromatography is carried out on a DEAE support. For factor IX enrichment, chromatography is usually carried out on a support having amino groups. In the isolation of factor VIII, chromatographic steps are usually carried out on a sorbent having ternary amino groups (e.g. DEAE) or having quaternary ammonium groups (e.g. TMAE) or else on hydrophobic separating materials.

Other examples of the separation of substances where the retention of the biological activity is particularly important are known to the person skilled in the art from the literature. In all of these cases, a particulate chromatographic support having a particular separation effector can be replaced by a membrane of the invention which comprises the same or a similar separation effector. Examples of membranes which comprise separation effectors of this type have already been given and are disclosed, in particular, in the following examples.

The following examples are intended to describe the subject of the invention in greater detail; they do not restrict the subject of the invention.

It is assumed that even without further details a person skilled in the art can make use of the above description to the fullest extent. The preferred embodiments are therefore to be understood solely as descriptive disclosure which on no account is in any way limiting.

The complete disclosure of all applications, patents and publications mentioned above and below, and of the corresponding application DE 1 95 01 726.9, submitted on Jan. 20, 1995, are incorporated into this application by reference.

EXAMPLES

Room temperature is taken below to mean a temperature of from 15° to 30° C.

Example 1

Introduction of C=C Bonds into a Polyamide in Aqueous Solution (Version A)

To carry out the synthesis, a polyamide fiber bundle of NYLON (fiber bundle of 64 fibers, 32 cm long, about 200 μm internal diameter, about 2 mm external diameter, mean pore diameter from 1–2 μm, surface area 97 cm²) is shortened to 30 cm and packed into a 300–10 mm SUPERFOR-MANCE® (E. Merck) chromatography column. An inert pump is connected to this column. The apparatus is firstly flushed with water. For the reaction, 20 g of glycidyl methacrylate are dissolved in 200 ml of 1M NaOH and circulated for two hours by a pump at a high rate (5 ml/min) at 40° C. The derivatized membrane is then rinsed with water.

Example 2

Introduction of C=C Bonds into a Polyamide (Aqueous-Organic Solution; Version B)

10 g of glycidyl methacrylate are dissolved in 200 ml of aqueous dimethylformamide (50% by volume) and circulated by a pump in the apparatus described in Example 1 (two hours at 60° C.). The derivatized hollow-fiber membrane is then rinsed with water.

Example 3

Introduction of C=C Bonds into a Polyamide (Aqueous-Organic Solution; Version C)

10 g of glycidyl methacrylate are dissolved in 200 ml of aqueous dimethyl sulfoxide (50% by volume) and circulated by a pump in the apparatus described in Example 1 (two hours at 60° C.). The derivatized hollow-fiber membrane is then rinsed with water.

Example 4

Introduction of C=C Bonds into a Polyamide (Aqueous-Organic Solution; Version D)

10 g of glycidyl methacrylate are dissolved in 200 ml of aqueous dimethylformamide (50% by volume in 0.5M sodium carbonate buffer, pH 10) and circulated by a pump in the apparatus described in Example 1 (two hours at 60° C.). The derivatized hollow-fiber membrane is then rinsed with water.

Example 5

Introduction of C=C bonds into a Polyamide (Aqueous-Organic Solution; Version E)

10 g of glycidyl methacrylate are dissolved in 200 ml of aqueous dimethylsulfoxide (50% by volume in 0.5M sodium carbonate buffer, pH 10) and circulated by a pump in the apparatus described in Example 1 (two hours at 60° C.). The derivatized hollow-fiber membrane is then rinsed with water.

Example 6

Introduction of C=C Bonds into a Polyamide (Aqueous-Organic Solution; Version F)

10 g of glycidyl methacrylate are dissolved in a mixture of 40 ml of dioxane and 160 ml of water, and 17.5 g of NaOH solution (32% by weight) are then added. This solution is then circulated by a pump in the apparatus described in Example 1 (flow rate 3 ml/min; one hour at 50° C.). The derivatized hollow fiber membrane is then rinsed with 100 ml of water, 200 ml of acetone and 100 ml of toluene.

Example 7

Introduction of C=C Bonds into a Flat Polyamide Membrane

Three layers of a flat polyamide membrane (each 0.3 mm thick; 12 cm diameter, 0.2 μm pore width) are clamped in a commercially available membrane holder and reacted with glycidyl methacrylate correspondingly to Example 6. The derivatized membrane is then rinsed with water.

Example 8

Graft Polymerization with Glycidyl Methacrylate

The hollow fiber membrane derivatized as in Example 1 is rinsed, in the apparatus described there, firstly with acetone, then with toluene (200 ml in each case). A solution of 20 g of glycidyl methacrylate and 1 g of azoisobutyronitrile (polymerization initiator) in 200 ml of toluene is then circulated by a pump at 80° C. for one hour. The derivatized hollow-fiber membrane is then rinsed with toluene and acetone.

Example 9

Graft Polymerization with Glycidyl Methacrylate

A solution of 15 g of glycidyl methacrylate and 1 g of azoisobutyronitrile(polymerization initiator) in 200 ml of toluene is circulated by a pump (7 ml/min) for one hour at 100° C. through the hollow-fiber membrane derivatized and rinsed as in Example 6, in the apparatus described in Example 1. The derivatized hollow-fiber membrane is then rinsed with toluene and acetone.

Example 10

Graft Polymerization with Acrylic Acid

The hollow-fiber membrane derivatized as in Example 1 is rinsed, in the apparatus described there, with [sic] firstly with acetone, then with toluene (200 ml in each case). A solution of 10 g of acrylic acid and 1 g of azoisobutyronitrile in 200 ml of toluene is then circulated by a pump at 80° C. for one hour. The derivatized hollow-fiber membrane is then washed with toluene, acetone and water and 1M NaOH.

Example 11

Graft Polymerization with a through-flow of Glycidyl Methacrylate

The hollow-fiber membrane derivatized as in Example 6 is rinsed, in the apparatus described there, with [sic] firstly with acetone, then with toluene (200 ml in each case). A solution of 20 g of glycidyl methacrylate and 1 g of azoisobutyronitrile (polymerization initiator) in 200 ml of toluene is prepared. A linear flow of this solution at 10 cm/min at 90° C. is pumped through the apparatus; this procedure takes about 20 minutes. The derivatized hollow-fiber membrane is then rinsed with toluene and acetone.

Example 12

Batch Graft Polymerization with Glycidyl Methacrylate 10 g of polyamide powder (mean particle size 200 μm, mean pore size 3 μm) are derivatized in a manner corresponding to that of Example 1. The derivatized polyamide powder is then reacted in a reaction solution of 20 g of glycidyl methacrylate and 1 g of azoisobutyronitrile (polymerization initiator) in 200 ml of toluene in a three-necked flask, with stirring, at 85° C. for three hours, and the reaction product is then rinsed with toluene and acetone.

Example 13

Graft Polymerization on a Derivatized Flat Membrane with a Through-Flow of Glycidyl Methacrylate The flat polyamide membranes derivatized as in Example 7 are reacted in a manner corresponding to that of Example 10 with a through-flow of a reaction solution of 200 g of glycidyl methacrylate and 10 g of azoisobutyronitrile (polymerization initiator) in 2 l of toluene, at 95° C. The derivatized membrane is then rinsed with toluene and acetone.

Example 14

Batch Graft Polymerization on a Derivatized Flat Membrane with Glycidyl Methacrylate The flat polyamide membranes derivatized as in Example 7 are wound onto a wire frame and reacted (1 hour) in a solution of 200 g of glycidyl methacrylate and 10 g of azoisobutyronitrile (polymerization initiator) in 2 l of toluene at 85° C., with stirring.

The derivatized membrane is then rinsed with toluene and acetone.

Example 15

Determination of the Density of Epoxy Groups

The density of epoxy groups in the membranes derivatized as in Examples 8, 11, 12, 13 and 14 is determined by perchloric acid titration in non-aqueous medium (M.Pribl; Fresenius Z. Anal. Chem. 303, 113-116; 1980)). For this, the hollow-fiber membrane derivatized as in the examples is cut into small pieces and about 1 g of the membrane pieces are titrated.

The following values were found (mmol epoxy groups g of membrane):

| Example: | 8 | 11 | 12 | 13 | 14 |
|---|---|---|---|---|---|
| mmol/g: | 1.0 | 1.5 | 0.3 | 0.5 | 0.13 |

Example 16

Modification of a Membrane to Give a Weakly Basic Anion Exchanger

The membrane derivatized as in Example 6 is first rinsed with water in the apparatus described in Example 1. 200 ml of an aqueous diethylamine solution (50% by volume) are then pumped through the apparatus at room temperature for 6 hours. The resultant ion-exchange membrane is finally washed with 0.5M sodium phosphate buffer (pH 7) until the eluate is neutral.

Example 17

Modification of a Membrane to Give a Support Activated with Azlactone Groups

The membrane derivatized as in Example 6 and membrane [sic] grafted with epoxypropyl methacrylate as in Example 9 is firstly rinsed with water in the apparatus described in Example 1. A solution of 12.4 g of sodium carbonate monohydrate in 200 ml of water is adjusted to pH 11 using concentrated HCl, and 30 g of sodium disulfide hydrate is dissolved in this solution. The solution is heated to 40° C. and pumped through a column maintained at 40° C. with a flow rate of 7 ml/min, for one hour. The column is then rinsed with 100 ml of water and 200 ml of acetone, and dried overnight at 50° C. in a vacuum drying cabinet.

40 g of vinyldimethylazlactone are dissolved in 200 ml of dimethylformamide and 3.3 g of 1,8-diazabicylclo(5,4,0)

undecen-7-ene [sic] are added. This solution is pumped through the apparatus at room temperature for 8 hours with a flow rate of 7 ml/min. The reaction is then continued overnight without pump circulation. The column is rinsed with 100 ml of dimethylformamide and extracted with ethyl acetate for two hours at 80° C.

Example 18

Modification of a Membrane to Give a Support with Phenol Ether Groups (for Hydrophobic Interaction Chromatography)

The membrane derivatized as in Example 6 and membrane [sic] grafted with epoxypropyl methacrylate as in Example 9 is firstly rinsed with water in the apparatus described in Example 1. 10 g of phenol are dissolved together with 24 g of sodium hydroxide solution (32% by weight) in 200 ml of water and pumped through the apparatus at 90° C. at a flow rate of 5 ml/min for 6 hours. The reaction is continued at room temperature overnight without pump circulation. Rinsing is then carried out using water, 1M sodium hydroxide solution, water, 0.1M phosphate buffer pH 7, water and acetone. The membranes are then dried overnight at room temperature in a vacuum drying oven.

Example 19

Modification of a Membrane to Give a Thiophilic Affinity Support

The membrane derivatized as in Example 6 and membrane [sic] grafted with epoxypropyl methacrylate as in Example 9 is firstly rinsed with water in the apparatus described in Example 1. 7.75 g of sodium carbonate monohydrate are dissolved in 125 ml of water and then 18.75 g of sodium hydrogen sulfide hydrate are added. The solution is heated to 40° C. and pumped through the apparatus at a flow rate of 3 ml/min for one hour. Rinsing is then carried out using 100 ml of water.

7.75 g of sodium carbonate monohydrate are dissolved in 125 ml of water, and 5 ml of divinylsulfone are added. The solution is heated to 40° C. and pumped through the apparatus at a flow rate of 3 ml/min for one hour. Rinsing is then carried out using 100 ml of water.

7.75 g of sodium carbonate monohydrate are dissolved in 125 ml of water, and 20 ml of mercaptoethanol are added. The solution is heated to 40° C. and pumped through the apparatus at a flow rate of 2.5 ml/min for one hour. Rinsing is then carried out using 100 ml of each of water, 1M sodium hydroxide solution, water, 1M HCl, water, 0.1M phosphate buffer (pH 7) and water. A final rinse is carried out using 200 ml of aqueous ethanol (20% by weight).

Example 20

Modification of a Membrane to Give a Strongly Basic Anion Exchanger

The membrane derivatized as in Example 6 and membrane [sic] grafted with epoxypropyl methacrylate as in Example 9 is firstly rinsed with water in the apparatus described in Example 1. 100 ml of aqueous trimethylamine solution (45% by weight; Cat. No. 821 177; Merck, Darmstadt) were diluted with 100 ml of water and pumped through the apparatus at room temperature for three hours at 5 ml/min; the reaction is then continued overnight without pump circulation. The membrane is rinsed with water, 1M sodium hydroxide solution, water, 0.1M phosphate buffer (pH 7), water and acetone, and dried overnight at room temperature in a vacuum drying cabinet.

Example 21

Modification of a Membrane to Give a Support having Amino Groups

The membrane derivatized as in Example 6 and membrane [sic] grafted with epoxypropyl methacrylate as in Example 9 is firstly rinsed with water in the apparatus described in Example 1. Aqueous ammonia solution (about 100 ml; 32% by weight) is charged to the apparatus which has been warmed to 30° C. Ammonia solution is added over the course of three hours, so that the apparatus remains completely filled. The outlet of the apparatus is then closed and the reaction is continued overnight at room temperature. The membrane is rinsed with water, 1M sodium hydroxide solution, water, 0.1M phosphate buffer (pH 7), water and acetone, and dried overnight at room temperature in a vacuum drying cabinet.

Example 22

Modification of a Membrane to Give a Cation Exchanger

The membrane derivatized as in Example 6 and membrane [sic] grafted with epoxypropyl methacrylate as in Example 9 is firstly rinsed with water in the apparatus described in Example 1. 10 g of sodium dihydrogen phosphate, 40 g of sodium sulfite and 10 g of tetrabutylammonium hydrogen sulfate are dissolved in 200 ml of water and adjusted to pH 8. This solution is heated to 95° C. and pumped through the apparatus for 2.5 hours at 7 ml/min. The membrane is rinsed with water, 1M sodium hydroxide solution, water, 0.1M phosphate buffer (pH 7), water and acetone, and dried overnight at room temperature in a vacuum drying cabinet.

Example 23

Modification of a Membrane to Give a Support for Metal Chelate Affinity Chromatography The membrane derivatized as in Example 6 and membrane [sic] grafted with epoxypropyl methacrylate as in Example 9 is firstly rinsed with water in the apparatus described in Example 1. 26 g of iminodiacetic acid are dissolved in 200 ml of water and adjusted to pH 11 using sodium hydroxide solution. The solution is heated to 60° C. and pumped through the apparatus at 5 ml/min for three hours; the reaction is then continued overnight at room temperature without pump circulation. The membrane is rinsed with water, 1M sodium hydroxide solution, water, 0.1M phosphate buffer (pH 7), water and acetone and dried overnight at room temperature in a vacuum drying cabinet.

Example 24

Determination of the Protein Binding Capacity 0.5 g of the membrane modified as in Example 16 and cut into small pieces is shaken in 10 ml of a solution of bovine serum albumin (5 mg/ml in 20 mM Tris pH 8.2) for 3 hours. The membrane pieces are filtered off with suction and the remainder is discarded. The bound protein is desorbed by treatment with 20 ml of a buffer solution of 20 mM Tris +1M sodium chloride pH 8. The content is determined photometrically at 280 mm.

The protein binding capacity is found to be 44 mg of protein/g of membrane.

We claim:

1. A shaped article comprising a polymer produced by:
   a) providing a shaped article consisting essentially of a polyamide;
   b) introducing polymerizable double bonds into said shaped article by reacting said polyamide with a compound which comprises both a polymerizable double bond and also an oxirane ring;
   c) polymerizing monomers onto the derivatived polyamide of a) whereby said monomers contain an epoxide radical, an azlactone radical, or a separation effector, resulting in a shaped article derivatized by polymer chains of said monomers;
   d) optionally reacting said epoxide radical or said azlactone radical to yield a separation effector, resulting in a shaped article useful for separation techniques.

2. As shaped article according to claim, wherein said shaped article consisting essentially of a polyamide of a) is porous.

3. A polymer produced by reacting a polyamide with a compound containing a polymerizable double bond and an oxirane ring to produce a derivatized polyamide and polymerizing monomers on to the derivatized polyamide, said monomers containing acrylic acid unit, an epoxide radical, an azlactone radical or a separation effector.

4. A polymer produced by polymerizing monomers onto a derivatized polyamide produced by reacting a polyamide with a compound containing a polymerizable double bond and an oxirane ring, said monomers containing acrylic acid units, an epoxide radical, an azlactone radical in a separation effector.

5. A shaped article according to claim 1, wherein the monomer of (c) comprises monomer units of formula II,

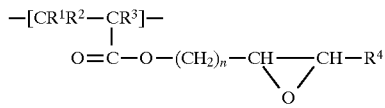

where $R_1$, $R^2$, and $R^3$ independently of one another are H or $CH_3$, $R^4$ is H, alkyl with from 1 to 5 carbon atoms or aryl with from 6 to 12 carbon atoms and n is an integer from 1 to 5.

6. A shaped article according to claim 1, wherein the monomer of (c) contains monomer units of formula V,

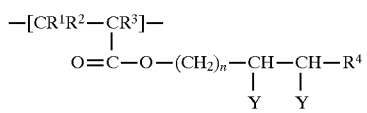

where $R^1$, $R^2$, and $R^3$ independently of one another are H or $CH_3$, $R^4$ is H, alkyl with from 1 to 5 carbon atoms or aryl with from 6 to 12 carbon atoms, n is an integer from 1 to 5, one radical Y is a radical of formula VI and the other radical Y is OH

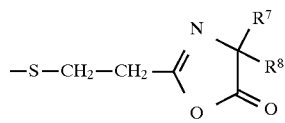

and $R^7$ and $R^8$ independently of one another are H or alkyl with from 1 to 5 carbon atoms.

7. A shaped article according to claim 1, wherein the monomer of (c) comprises monomer units of formula III

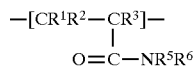

where $R^1$, $R^2$ and $R^3$ independently of one another are H or $CH_3$, $R^5$ is H, or alkyl with from 1 to 5 carbon atoms substituted with —COOH, with —$SO_3H$ or with $NR^7R^8$, or aryl with from 6 to 12 carbon atoms and substituted with —COOH, —$SO_3H$ or with —$NR^7R^8$, $R^6$ is alkyl with from 1 to 5 carbon atoms substituted with —COOH, with —$SO_3H$ or with $NR^7R^8$, or aryl with from 6 to 12 carbon atoms and substituted with —COOH, —$SO_3H$ or —$NR^7R^8$, where $R^5$ and $R^6$ are selected so that either both radicals are acid or basic or one of the radicals is neutral, and $R^7$ and $R^8$ independent or one another are H or alkyl with from 1 to 5 carbon atoms.

8. A shaped article according to claim 5, wherein the monomer of (c) comprises monomer units of the formula IV,

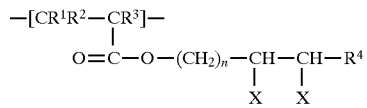

where $R^1$, $R^2$ and $R^3$ independently of one another are H or $CH_3$, $R^4$ is H, alkyl with from 1 to 5 carbon atoms or aryl with from 6 to 12 carbon atoms, n is an integer from 1 to 5, one radical X is a separation effector and the other radical X is OH.

9. A shaped article according to claim 1 wherein the compound having a polymerizable double bond and an oxirane ring is a compound of formula I,

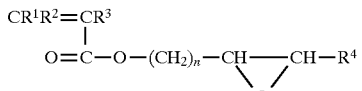

where $R_1$, $R^2$, and $R^3$ independently of one another are H or $CH_3$, $R^4$ is H, alkyl with from 1 to 5 carbon atoms or aryl with from 6 to 12 carbon atoms and n is an integer from 1 to 5.

10. A shaped article according to claim 1, wherein the monomer of compounds is acrylic acid.

11. A shaped article according to claim 8, wherein the separation effector is an ionic radical selected from the group consisting of —$PO_4H_2$, —$NR^7R^8$ and $N^+R^7R^8R^9$, where R$^7$ and R$^8$ independently of one another are H or alkyl with from 1 to 5 carbon atoms and R$^9$ is alkyl with from 1 to 5 carbon atoms with the proviso that if X=—N$^+$R$^7$R$^8$R$^9$, R$^7$ and R$^8$ may not be H.

12. A shaped article according to claim 8, the separation effector is a hydrophobic moiety —OR$^{10}$ or —NHR$^{10}$, where R$^{10}$ is C$_1$–C$_{20}$-alkyl, C$_6$–C$_{25}$-aryl, C$_7$–C$_{25}$-alkylaryl or C$_7$–C$_{25}$-arylalkyl, and where these radicals may also be derivatized with nitrile or C$_1$–C$_5$-alkoxy, and where, furthermore, one or more non-adjacent CH$_2$ radicals may also be replaced by NH or O or else one or more CH radicals may be replaced by N.

13. A shaped article according to claim 8, wherein the separation effector is a metal chelate affinity group.

14. A shaped article according to claim 8, wherein the separation effector is a thiophilic radical.

15. An affinity support prepared from a shaped article according to claim 1.

16. An immobilized enzyme prepared from shaped article according to claim 1.

17. A shaped article on which an affinity ligand or an enzyme is immobilized, prepared from a graft polymer according to claim 3.

* * * * *